US009657326B2

(12) United States Patent
Ruether et al.

(10) Patent No.: US 9,657,326 B2
(45) Date of Patent: May 23, 2017

(54) METHOD OF DIAGNOSING PNEUMONIA BY DETECTING A VOLATILE ORGANIC COMPOUND

(71) Applicant: MEON Medical Solutions GmbH & Co. KG, Graz (AT)

(72) Inventors: Horst Ruether, Hart bei Graz (AT); Anton Amann, Goetzens (AT)

(73) Assignee: MEON Medical Solutions GmbH & Co. KG, Graz (AT)

( * ) Notice: Subject to any disclaimer, the term of this patent is extended or adjusted under 35 U.S.C. 154(b) by 0 days.

(21) Appl. No.: 14/362,509

(22) PCT Filed: Dec. 3, 2012

(86) PCT No.: PCT/EP2012/074239
§ 371 (c)(1),
(2) Date: Jun. 3, 2014

(87) PCT Pub. No.: WO2013/083518
PCT Pub. Date: Jun. 13, 2013

(65) Prior Publication Data
US 2014/0336080 A1    Nov. 13, 2014

(30) Foreign Application Priority Data
Dec. 6, 2011 (EP) ...................................... 11009630

(51) Int. Cl.
*G01N 33/497* (2006.01)
*C12Q 1/14* (2006.01)
(Continued)

(52) U.S. Cl.
CPC ................. *C12Q 1/14* (2013.01); *C12Q 1/04* (2013.01); *G01N 33/497* (2013.01);
(Continued)

(58) Field of Classification Search
CPC .......... C12Q 1/04; C12Q 1/14; G01N 33/497; G01N 2800/26; G01N 2033/4977;
(Continued)

(56) References Cited

U.S. PATENT DOCUMENTS 4,349,626 A     9/1982 Labows et al.
2005/0085740 A1*  4/2005 Davis et al. ................... 600/532
(Continued)

FOREIGN PATENT DOCUMENTS

WO    WO-2009054913 A1    4/2009
WO    WO-2010045458 A1    4/2010

OTHER PUBLICATIONS

Savelev et al. (Letters in Applied Microbiology, 2011, 52:610-613).*
(Continued)

*Primary Examiner* — Jeremy C Flinders
(74) *Attorney, Agent, or Firm* — Clark & Elbing LLP

(57) ABSTRACT

The present invention relates to a method of diagnosing an existing or developing acute pneumonia induced by a microorganism by detecting one or more volatile organic compound(s) in a subject's sample and the use of one or more volatile organic compound(s) for the detection of *Staphylococcus aureus*, *Pseudomonas aeruginosa*, *Streptococcus pneumoniae* or *Haemophilus influenza* and optionally opportunistic pathogen *Candida albicans*.

21 Claims, 1 Drawing Sheet

(51) Int. Cl.
*C12Q 1/04* (2006.01)
*C12Q 1/10* (2006.01)

(52) U.S. Cl.
CPC . *G01N 2033/4977* (2013.01); *G01N 2333/21* (2013.01); *G01N 2333/285* (2013.01); *G01N 2333/31* (2013.01); *G01N 2333/315* (2013.01); *G01N 2333/3156* (2013.01); *G01N 2800/26* (2013.01)

(58) Field of Classification Search
CPC ..... G01N 2333/285; G01N 2333/3156; G01N 2333/21; G01N 2333/31; G01N 2333/315
See application file for complete search history.

(56) References Cited

U.S. PATENT DOCUMENTS

| | | |
|---|---|---|
| 2009/0230300 A1 | 9/2009 | Trevejo et al. |
| 2009/0239252 A1 | 9/2009 | Trevejo et al. |
| 2010/0121210 A1 | 5/2010 | Lindner et al. |
| 2014/0370542 A1* | 12/2014 | Suslick et al. ............... 435/36 |

OTHER PUBLICATIONS

S. Van den Velde et al. / J. Chromatogr. B 875 (2008) 344-348.*
Baumbach et al. (From Breath Analysis for Clinical Diagnosis and Therapeutic Monitoring, Editors Anton Amman and David Smith, 2005, ISBN 981-256-284-2, "Metabolites in Human Breath: Ion Mobility Spectrometers as Diagnostic Tools for Lung Diseases" by Baumbach et al., pp. 53-66).*
Hockstein et al., "Diagnosis of pneumonia with an electronic nose: correlation of vapor signature with chest computed tomography scan findings," Laryngoscope 114(10):1701-5 (2004).
Zechman et al., "Characterization of pathogenic bacteria by automated headspace concentration-gas chromatography," J Chromatogr. 377:49-57 (1986).
International Search Report for International Patent Application No. PCT/EP2012/074239, mailed Apr. 9, 2013 (6 pages).
Written Opinion of the International Searching Authority for International Patent Application No. PCT/EP2012/074239, mailed Apr. 9, 2013 (7 pages).
International Preliminary Report on Patentability for International Patent Application No. PCT/EP2012/074239, issued Jun. 10, 2014 (8 pages).

* cited by examiner

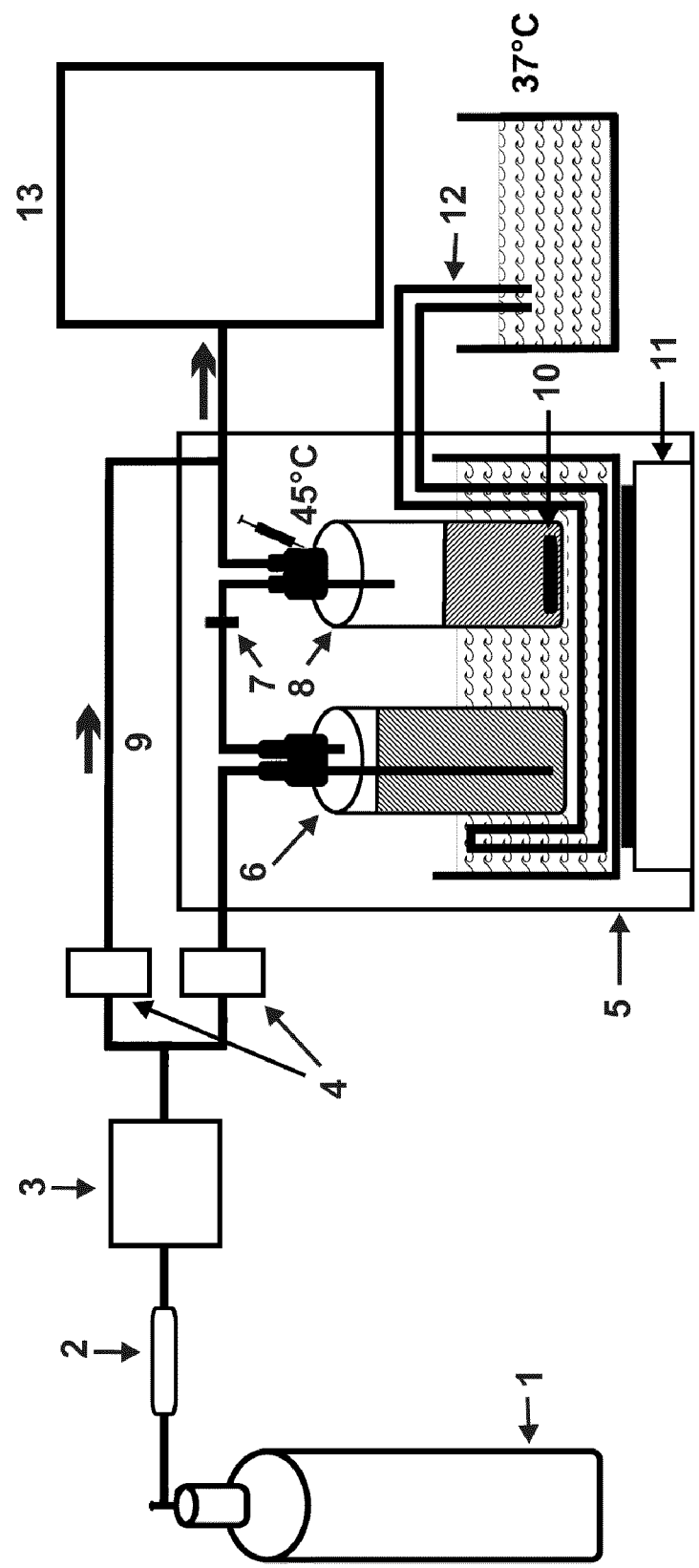

METHOD OF DIAGNOSING PNEUMONIA BY DETECTING A VOLATILE ORGANIC COMPOUND

CROSS-REFERENCE TO RELATED APPLICATIONS

This application is a national phase of International Application No. PCT/EP2012/074239, filed Dec. 3, 2012, which claims priority from European Application No. EP 11009630.2, filed Dec. 6, 2011, both hereby incorporated by reference.

The present invention relates to a method of diagnosing an existing or developing acute pneumonia induced by a microorganism by detecting one or more volatile organic compound(s) in a subject's sample and the use of one or more volatile organic compound(s) for the detection of *Staphylococcus aureus, Pseudomonas aeruginosa, Streptococcus pneumoniae* or *Haemophilus influenza* and optionally opportunistic pathogen *Candida albicans*.

Pneumonia is a common illness affecting approximately 450 million people a year and occurring in all parts of the world. It is a major cause of death among all age groups resulting in 4 million deaths (7% of the world's yearly total). Rates are greatest in children less than five, and adults older than 75 years of age.

Pneumonia is an inflammatory condition of the lung, especially of the alveoli (microscopic air sacs in the lungs), associated with fever, chest symptoms, and consolidation on a chest radiograph. Patients suffering from infectious pneumonia often have a productive cough, fever accompanied, shortness of breath, sharp or stabbing chest pain during deep breaths, confusion, and an increased respiratory rate. Pneumonia can be classified in several ways. It is most commonly classified by where or how it was acquired (community-acquired, aspiration, healthcare-associated, hospital-acquired, and ventilator-associated pneumonia), but may also be classified by the area of lung affected (lobar pneumonia, bronchial pneumonia and acute interstitial pneumonia), or by the causative organism.

Pneumonia is primarily due to infections, with less common causes including irritants and the unknown reasons. Although more than one hundred strains of microorganisms can cause pneumonia, only a few are responsible for most cases. The most common types of infectious agents are viruses and bacteria with it being less commonly due to fungi or parasites. A causative agent is not isolated in approximately half of cases despite careful testing. The term pneumonia is sometimes more broadly applied to inflammation of the lung (for example caused by autoimmune disease, chemical burns or drug reactions), however this is more accurately referred to as pneumonitis.

Bacteria are the most common cause of community acquired pneumonia, with *Streptococcus pneumoniae* isolated in nearly 50% of cases. Other commonly isolated bacteria include: *Haemophilus influenzae, Chlamydophila pneumoniae, Mycoplasma pneumoniae, Staphylococcus aureus, Moraxella catarrhalis, Legionella pneumophila* and gram-negative bacilli.

From the above, it follows that it is important to clearly identify pneumonia (existing or developing) in a reliable as well as time- and cost-efficient manner as early as possible.

It has been suggested to identify *Staphylococcus aureus, Klebsiella pneumonia* (WO 2009/054913) and *Escherichia coli* (US 2009/0230300) by detecting a series of volatile organic compounds (VOCs) in body fluids or respiratory gases. However, the VOCs suggested in WO 2009/054913 (corresponding to US 2009/0230300) are not specific enough for these pneumonia-causing bacterial species, since they are also released by non-pathogenic bacteria. This does mean that the known published VOCs are also present in a healthy person and therefore are not specific for pneumonia-causing microorganisms.

For pneumonia, in particular ventilator-associated pneumonia (VAP), no reliable early diagnostic is available. At a later stage, imaging diagnostic techniques could be used in order to detect pneumonia, particularly if pneumonia is suspected. A bacterial infection presents itself to the physician by a reaction of the immune system, e.g., by fever. For patients at the intensive care unit, with tubes and cables being omnipresent, imaging diagnostic techniques are not easily applicable due to transport problems.

Accordingly, it was an object of the present invention to provide a method allowing for the diagnosis of pneumonia induced by a microorganism in a reliable as well as time- and cost-efficient manner as early as possible.

Surprisingly, it was found that there are VOCs which are indicative for existing or developing microorganism-induced pneumonia and which are not present in healthy subjects. A variety of VOCs has been identified in the headspace of bacterial cultures (see Example). These VOCs are not known to be present in healthy, i.e. uninfected, subjects. For the detection, a GC-MS (gas chromatography with mass spectroscopic detection) was used as detection device.

Accordingly, in a first aspect the present invention relates to a method of diagnosing an existing or developing acute pneumonia induced by a microorganism by detecting one or more volatile organic compound(s) in a subject's sample, wherein the presence of the one or more volatile organic compound(s) (VOCs) in the sample is indicative of the existing or developing acute pneumonia.

Alternatively or additionally, the present invention relates to a method for determining if a patient has an enhanced risk/probability an existing or developing acute pneumonia induced by a microorganism by detecting one or more volatile organic compound(s) in a subject's sample, wherein the presence of the one or more volatile organic compound(s) (VOCs) in the sample is indicative of the existing or developing acute pneumonia. The below details, definitions and comments relate to both methods. The feature "enhanced risk/probability" shall mean that it is more likely for the patient to have or develop an acute pneumonia induced by a microorganism as compared to a healthy person or a person non-infected by the respective microorganism.

Volatile organic compounds are organic chemicals that have a nonzero vapor pressure at room-temperature (higher than 1 part-per-trillion, 1 ppt). Their vapor pressure results from a comparatively low boiling point, which causes large numbers of molecules to evaporate from the liquid or solid form of the compound and enter the surrounding air. An organic compound is any member of a large class of gaseous, liquid, or solid chemical compounds whose molecules contain carbon. In a preferred embodiment a VOC is any organic compound having an initial boiling point less than or equal to 350, particularly 300° C., measured at a standard atmospheric pressure of 101.3 kPa. Particularly, it has a boiling point in the range of 50 to 250° C.

Acute pneumonia does appear in contrast to chronic pneumonia spontaneously. For example, nosocomial pneumonia (hospital acquired pneumonia) does usually appear spontaneously between 2 days after hospitalization and up to 14 days post hospitalization. A special form is the VAP (ventilator-associated pneumonia). Common pathogens are *Pseudomonas aeruginosa, Staphylococcus aureus, Streptococcus pneumonia* and *Haemophilus influenza* (see Koulenti et al., Crit Care Med 37, 2360 ff, 2009). There are also further pathogens, e.g. of the category of Enterobacteriacea. The support of insufficient spontaneous breathing by artificial respiratory equipment is of great importance, but is also a great burden for the patient and favors pneumonia. With a likelihood of 30% ventilated critical ill patients get a VAP (ventilator associated pneumonia). The mortality of these patients is about 30%. The disease typically is compared with a bacterial colonization of the lung.

Existing acute pneumonia is characterized by typical symptoms as known by the skilled person, e.g. fever, ague or sanious mucus.

Developing acute pneumonia is characterized by an increased number of bacteria but no typical symptoms at this status.

The detection of one or more volatile organic compound(s) from breath samples can be done with air-bags, glass tubes filled with suitable absorbent(s) or by on-line measurement. Body fluid sampling can be done with syringes or vacutainer and bacteria may be grown in media or in culture before VOCs can be measured from the headspace. To detect VOCs technologies like GC-MS (gas chromatography-mass spectroscopy), IMS (ion mobility spectrometry) or PTR-TOF-MS (proton transfer reaction-time-of-flight mass spectroscopy) can be used.

"Diagnosing pneumonia" in the context of the present invention has a broad meaning. In the medical field, it is used for a process of attempting to determine and/or identify a possible disease. The diagnosing may be done in order to clarify whether or not a subject is diseased. Alternatively or additionally, the extent of the disease may be determined. Accordingly, it may or may not be known whether the subject is already suffering from a disease or is developing a disease, presently being still without typical symptoms. In one alternative, it could be checked whether a subject is suffering from pneumonia. The diagnosis is carried out in order to determine whether the subject is healthy, already suffering from or developing pneumonia. If the subject is suffering from pneumonia, the degree and extent of the disease as well as the microorganism causing the disease could be determined, too. In a second alternative, it is known that the subject is or was diseased. The method could be used in the monitoring of the health status of a previously or still diseased subject. This could be done in the context of the monitoring of a therapy, e.g. with antibiotics.

A "microorganism" is an organism that is unicellular or lives in a colony of cellular organisms. In the context of the present invention the microorganism is capable of causing pneumonia, particularly acute pneumonia. The term microorganism therefore includes bacteria and fungi. Please note that viruses are not included. Typical examples of bacteria capable of causing pneumonia, particularly acute pneumonia are without limitation Bacteria are the most common cause of community acquired pneumonia, with *Streptococcus pneumoniae* isolated in nearly 50% of cases. Other commonly isolated bacteria include: *Haemophilus influenzae* in 20%, *Chlamydophila pneumoniae* in 13%, *Mycoplasma pneumoniae* in 3%, *Staphylococcus aureus, Moraxella catarrhalis, Legionella pneumophila, Chlamydia psittaci, Coxiella burnetti,* and *Pseudomonas aeruginosa*. Fungal pneumonia is most often caused by *Histoplasma capsulatum, blastomyces, Cryptococcus neoformans, Pneumocystis jiroveci,* and *Coccidioides immitis*. Due to the higher relevance, the microorganism is capable of causing pneumonia, particularly acute pneumonia is preferably a bacterial microorganism.

As detailed above, one or more volatile organic compound(s) are detected in a subject's sample. As used herein the term "subject" can mean either a human or non-human animal, preferably vertebrates such as mammals, especially primates, such as humans. The sample may be a gaseous, solid or liquid sample, for example from a bodily source. The source may be, for example, a tissue or fluid or gas (e.g. respiratory air, urine, sweat, blood, sputum, and/or exhaled breath condensate) from a body. However, respiratory air is preferred.

The sampling can be done manually and transported to an IVD-measurement system or the measurement system is connected with the patient and an on-line sampling or interval sampling can be done.

In case of in-vitro measurements manual sampling is typically done with syringes or vacutainer to collect body fluids like blood. For the sampling of VOCs from breath air-bags or glass tubes with suitable adsorbents (e.g., thermodesorption tubes) are used.

In case of ex-vivo or in vivo measurements (as far as allowed by the respective patent law), the analyzer is connected typically with an artery or venous blood vessel or in case of breath with a respiratory mask or a tube is placed within the nose.

In accordance with the present invention, the presence of the one or more volatile organic compound(s) (VOCs) in the sample is indicative of the existing or developing acute pneumonia. This means that the one or more volatile organic compound(s) indicative of the existing or developing acute pneumonia is/are not present in a subject's sample not infected with a microorganism inducing pneumonia, particularly not infected with one of the major pneumonia inducing bacteria, namely *Pseudomonas aeruginosa, Staphylococcus aureus, Streptococcus pneumoniae* and *Haemophilis influenza*. Accordingly, the VOCs in the sample (optionally after having been cultivated to increase number or metabolites of the microorganism) is specific for the microorganism and therefore it can be concluded that the subject is infected with one or more microorganisms causing pneumonia, if one or more VOCs are present in the sample. The skilled person will understand that "not present" means that the respective VOC is at a background level characteristic for the respective method of detecting the VOC or cannot be detected at all.

Preferably, the volatile organic compound is selected from the group consisting of 2-ethylacrolein, 2-methyl-2-butenal (Z), ethyl formate, ethyl isovalerate, isopentyl acetate, hydroxyacetone, 2-butanol, 2-methylbutyl 2-methylbutyrate, 2-methylbutyl isobutyrate, amyl isovalerate, ethyl 2-methylbutyrate, isoamyl butyrate, methyl 2-methylbutyrate, 1,10-undecadiene, 10-methyl-1-undecene, 1-decene, 1-nonene, 1-vinyl aziridine, mercaptoacetone, 3-phenylfuran, 3-(methylthio)propanal, o-hydroxybenzaldehyde, methyl propionate, vinyl butyrate, 2-acetyl-1,4,5,6-tetrahydropyridine, S-methyl thioacetate, 3-methyl-1-butanol, 2-nonanone, 3-(ethylthio)-propanal, 1-butanol, DMTS, methyl methacrylate, and dimethyldisulfide (see also following table).

| Compound | CAS |
| --- | --- |
| 2-methyl-1-propanol | 78-83-1 |
| 2-Ethylacrolein | 922-63-4 |
| 2-Methyl-2-butenal (Z) | 1115-11-3 |
| Ethyl formate | 109-94-4 |

-continued

| Compound | CAS |
| --- | --- |
| Ethyl isovalerate | 108-64-5 |
| Isopentyl acetate | 123-92-2 |
| Hydroxyacetone | 116-09-6 |
| 2-butanol | 78-92-2 |
| 2-Methylbutyl 2-methylbutyrate | 2445-78-5 |
| 2-Methylbutyl isobutyrate | 2445-69-4 |
| amyl isovalerate | 25415-62-7 |
| Ethyl 2-methylbutyrate | 868-57-5 |
| Isoamyl butyrate | 106-27-4 |
| Methyl 2-methylbutyrate | 868-57-5 |
| 1,10-Undecadiene | 13688-67-0 |
| 10-methyl-1-undecene | 22370-55-4 |
| 1-Decene | 872-05-9 |
| 1-Nonene | 124-11-8 |
| 1-Vinyl aziridine | 5628-99-9 |
| 2-Methoxy-5-Methylthiophene | 31053-55-1 |
| Mercaptoacetone | 24653-75-6 |
| 3-Phenylfuran | 13679-41-9 |
| 3-(Methylthio)propanal | 3268-49-3 |
| o-Hydroxybenzaldehyde | 90-02-8 |
| Methyl Propionate | 554-12-1 |
| Vinyl butyrate | 123-20-6 |
| 2-Acetyl-1,4,5,6-tetrahydropyridine | 25343-57-1 |
| S-Methyl thioacetate | 1534-08-3 |
| 3-Methyl-1-butanol | 123-51-3 |
| 2-nonanone | 821-55-6 |
| 3-(ethylthio)-propanal | 5454-45-5 |
| 1-Butanol | 71-36-3 |
| DMTS | 3658-80-8 |
| Methyl methacrylate | 80-62-6 |
| Dimethyldisulfide | 624-92-0 |

It is evident to the skilled person that the significance of the diagnosis increases with the number of these compounds detected. Accordingly, preferably at least 2, 3, 4, 5, 6, 7, 8, 9 or 10 VOCs, particularly those listed above, are detected in the method of the present invention.

Preferable, the method of the present invention comprises the following steps:
a) collecting a subject's sample suspected of comprising (i) one or more volatile organic compounds indicative of pneumonia and not present in a healthy subject or (ii) at least one of the pneumonia-causing bacteria *Staphylococcus aureus, Pseudomonas aeruginosa, Streptococcus pneumoniae* or *Haemophilus influenzae*;
b) optionally culturing the sample, if at least one of the pneumonia-causing bacteria is comprised in the sample;
c) detecting the presence of the one or more volatile organic compound(s); and
d) determining whether the subject is diseased or at risk of developing a pneumonia.

Step a) may be carried out as follows:

The collecting of samples is well known to the skilled person. For breath, the sampling, e.g. at the intensive care unit, can be done manually with an air-bag or a glass tube. In case of an air-bag a gas tight pouch with typical 1-2 liter volume can be used to collect breath. In case of a glass tube VOCs of the breath are adsorbed on a suitable adsorbent, contained in an appropriate device such as a thermodesorption tube. For a direct monitoring of VOCs, breath will be aspirated by or injected in analytical instrument, such as a proton-transfer-reaction time-of-flight mass spectrometer or ion mobility spectrometer and preferably be measured immediately without any intermediate step. If no real-time analytic is needed also gas chromatography-mass spectrometry is suitable.

If bacteria shall be identified from body fluids, like whole blood, plasma, saliva, pleura fluid or other body fluids, typically it is necessary to increase the number of bacteria. Therefore, a culture or media might be needed before VOCs can be measured, e.g. with the technologies described for breath.

Step b) is a facultative step, which may or may not be carried out. In step b) the sample may be cultured, if at least one of the pneumonia-causing bacteria is comprised in the sample. The step of culturing is usually intended to increase the amount of VOCs. Suitable methods for culturing microorganisms are well known to the person skilled in the art. Briefly, the cells of the microorganism are grown and maintained under conditions conducive to the culture of the cell. This includes an appropriate temperature and gas mixture (typically 37° C.), optionally in a cell incubator. Culture conditions may vary and are known to the skilled practitioner. Aside from temperature and gas mixture, the most commonly varied factor in cell culture systems is the medium. Recipes for media can vary in pH, glucose concentration and the presence of other nutrient components among others.

With respect to step c), please see above.

Finally, the determining of step d) may be carried out as follows:

The determination of concentrations from samples, e.g. breath samples or the headspace of cultures, may be carried out by different analytical techniques, as e.g., gas chromatography combined with mass spectrometric detection (GC-MS), proton transfer reaction mass spectrometry (PTR-MS), selected ion flow tube mass spectrometry (SIFT-MS), ion mobility spectrometry (IMS), laser spectroscopy, electronic nose or photo acoustic spectroscopy, as known to the skilled person. Each technology has advantages and disadvantages because of different attributes like time to result, sensitivity, selectivity, dimension (size) or cost. So it depends on the application which technology would be fit best and the skilled person is capable of selecting a suitable method.

In a preferred embodiment, the existing or developing acute pneumonia is hospital acquired pneumonia. With a likelihood of 30% ventilated critically ill patient will get a hospital or ventilator associated pneumonia (VAP). The mortality of these patients is about 30%. The disease typically is accompanied with a bacterial colonization of the lung.

In a very preferred embodiment of the present invention, the microorganism is *Pseudomonas aeruginosa, Staphylococcus aureus, Streptococcus pneumoniae* or *Haemophilis influenza*. The bacteria listed above responsible for the majority of infectious pneumonia. About 80% of all ventilator associated pneumonias are due to an infection with *Staphylococcus aureus, Pseudomonas aeroginosa, Streptococcus pneumoniae* and/or *Haemophilus influenza*.

In an even more preferred embodiment the VOC detected in the sample is indicative for the bacteria with which the subject is infected. Accordingly, if any of the VOCs listed below is found in a sample, it may be concluded with which bacterium/bacteria the subject from which the sample is derived is infected. In the Example section (see table) and in the following VOCs are categorized according to the bacterium/bacteria for which they are indicative:
a) The presence of one or more volatile organic compound(s) selected from the group consisting of 2-methyl-1-propanol, 2-ethylacrolein, 2-methyl-2-butenal (Z), ethyl formate, ethyl isovalerate, isopentyl acetate and hydroxyacetone is indicative of the presence of *Staphylococcus aureus*.
b) The presence of one or more volatile organic compound(s) selected from the group consisting of 2-butanol, 2-methylbutyl 2-methylbutyrate, 2-methylbutyl isobutyrate, amyl isovalerate, ethyl 2-methylbutyrate, isoamyl butyrate, methyl 2-methylbutyrate, 1,10-undecadiene, 10-methyl-1-undecene, 1-decene, 1-nonene, 1-vinyl aziridine, 2-methoxy-5-methylthiophene and mercaptoacetone is indicative of the presence of *Pseudomonas aeruginosa*.

c) The presence of one or more volatile organic compound(s) selected from the group consisting of 3-phenylfuran and 3-(methylthio)propanal is indicative of the presence of *Streptococcus pneumonia*.

d) The presence of one or more volatile organic compound(s) selected from the group consisting of o-hydroxybenzaldehyde, methyl propionate, vinyl butyrate, 2-acetyl-1,4,5,6-tetrahydropyridine and S-methyl thioacetate is indicative of the presence of *Haemophilus influenza*.

e) The presence of the volatile organic compound 3-methyl-1-butanol is indicative of the presence of *Staphylococcus aureus* and/or *Pseudomonas aeruginosa*.

f) The presence of the volatile organic compound 2-nonanone is indicative of the presence of *Pseudomonas aeruginosa* and/or *Streptococcus pneumonia*.

g) The presence of the volatile organic compound 3-(ethylthio)-propanal is indicative of the presence of *Pseudomonas aeruginosa* and/or *Haemophilus influenza*.

h) The presence of the volatile organic compound 1-butanol is indicative of the presence of *Staphylococcus aureus, Streptococcus pneumoniae* and/or *Haemophilus influenza*.

i) The presence of the volatile organic compound dimethyltrisulfide (DMTS) is indicative of the presence of *Pseudomonas aeruginosa, Streptococcus pneumoniae* and/or *Haemophilus influenza*.

j) The presence of one or more volatile organic compound(s) selected from the group consisting of methyl methacrylate and dimethyldisulfide is indicative of the presence of; *Staphylococcus aureus, Pseudomonas aeruginosa, Streptococcus pneumoniae* and/or *Haemophilus influenza*.

In a preferred embodiment of the present invention, the method further comprises detecting the presence of *Candida albicans*, particularly by detecting the presence of ethyl butyrate, isopentyl propionate, 2-methylbutyl acetate and/or vinyl ethyl ether. *Candida* is known to be an opportunistic pathogen commonly occurring as a result of an existing pneumonia. Also *Candida albicans* may be detected by means of VOCs, particularly by one or more of the following:

| Compound | CAS |
| --- | --- |
| Ethyl butyrate | 105-54-4 |
| Isopentyl propionate | 106-27-4 |
| 2-methylbutyl acetate | 624-41-9 |
| Vinyl ethyl ether | 109-92-2 |

As detailed above, the sample may be any sample from a subject in which VOCs (optionally after cultivation) may be detected. Preferably, the sample is selected from the group consisting of respiratory air, saliva, sputum, blood, plasma, urine, pleural fluid and pleural biopsy tissue.

Respiratory air is particularly suitable for the detection of VOCs, especially in case of infectious disease of the lung. Respiratory air contains a high number of VOCs which reflect the metabolism of normal cells but also microorganisms present in the subject or patient. Accordingly, body fluids like saliva, pleural fluid, blood and plasma could also be used in the detection of pneumonia.

In one embodiment of the present invention, the gaseous phase above a bacteria culture from the sample is analyzed, particularly wherein the sample is selected from the group consisting of saliva, sputum, blood, plasma, urine, pleural fluid, and pleural biopsy tissue. Depending on the sensitivity of the used technology and the number of bacteria within the same a direct detection of VOCs in the head space over the sample could be possible. To increase the detection limit a culture could be used to increase the number of bacteria first.

The subject may be any subject suspected or known to suffer from pneumonia or developing the same. Preferably, the subject is a mammal, particularly a human.

In a preferred embodiment the amount or pattern of the one or more volatile organic compounds is detected, wherein the amount or pattern is indicative of the degree of the pneumonia.

To detect a developing or an existing pneumonia the detection of only one of the listed VOCs is necessary and independent of the amount. But to increase the sensitivity and specificity it is favorable to detect a pattern of VOCs (i.e. the composition of VOCs and/or their amounts relative to each other). The pattern also enables to select between the mentioned bacteria (see Example).

With progression of the pneumonia the number of bacteria is increasing. Therefore the amount of VOCs is increasing in general and can be used as a first indicator of the degree of the pneumonia if the signal is monitored, because there is a variation of the amount over the time and VOCs can be compensated based on the metabolism processes of bacteria.

In a preferred embodiment, the detecting of the compound is performed using a differential mobility, as detailed above.

The method as specified above may further comprise the following step:

e) detecting the presence of at least one bacterium selected from the group of *Staphylococcus aureus, Pseudomonas aeruginosa, Streptococcus pneumoniae* and *Haemophilus influenzae* using method not involving VOCs.

In order to confirm the presence of a particular microorganism or to define the microorganism having infected the subject, a further detecting step may be carried out (cf. step e)). For this any suitable method known to the skilled person may be used. Suitable methods include DNA-based methods (e.g. involving PCR), immunoassay-based methods or immune latex agglutination-based methods. Determining the specific microorganism may be a prerequisite in the selection of a suitable therapy for the subject, e.g. by selecting a suitable antibiotic.

In another aspect, the present invention relates to the use of one or more volatile organic compound(s) selected from the group consisting of 2-ethylacrolein, 2-methyl-2-butenal (Z), ethyl formate, ethyl isovalerate, isopentyl acetate, hydroxyacetone, 2-butanol, 2-methylbutyl 2-methylbutyrate, 2-methylbutyl isobutyrate, amyl isovalerate, ethyl 2-methylbutyrate, isoamyl butyrate, methyl 2-methylbutyrate, 1,10-undecadiene, 10-methyl-1-undecene, 1-decene, 1-nonene, 1-vinyl aziridine, mercaptoacetone, 3-phenylfuran, 3-(methylthio)propanal, o-hydroxybenzaldehyde, methyl propionate, vinyl butyrate, 2-acetyl-1,4,5,6-tetrahydropyridine, S-methyl thioacetate, 3-methyl-1-butanol, 2-nonanone, 3-(ethylthio)-propanal, 1-butanol, DMTS, methyl methacrylate, and dimethyldisulfide for the detection of *Staphylococcus aureus, Pseudomonas aeruginosa, Streptococcus pneumoniae* or *Haemophilus influenza*.

In accordance with the present invention any of the VOCs listed above may be used in the detection of *Staphylococcus aureus, Pseudomonas aeruginosa, Streptococcus pneumoniae* or *Haemophilus influenza*. The presence of any of the VOCs in a sample in which normally the VOC is not present is indicative of the above bacteria. Optionally one or more volatile organic compound(s) selected from the group consisting of ethyl butyrate, isopentyl propionate, 2-methylbutyl acetate and vinyl ethyl ether may additionally be used for the detection of *Candida albicans*.

Above in the context of the method of the present invention, details are given on how the presence of specific VOCs may be used in order to detect *Staphylococcus aureus, Pseudomonas aeruginosa, Streptococcus pneumoniae* and/or *Haemophilus influenza* (see items a) to j)).

The VOC(s) may be detected in a solid or liquid or gaseous sample, for example from a bodily source, from an environmental source, and/or from an industrial source. The source may be, for example, a tissue or fluid or gas (e.g. respiratory air, urine, sweat, blood, sputum, and/or condensate) from a body, a water or soil sample, and/or an industrial product or waste stream sample. The sample to be analyzed may be collected and analyzed as known to the skilled person and as detailed above.

Furthermore, the use may be further characterized as detailed in the context of the method of the present invention.

FIGURES

FIG. 1 shows a scheme of the device used for bacteria culture experiments and VOC analyses. The device comprises one 50 l gas cylinder fermenter 1 (synthetic air), Supelcarb™ hydrocarbon trap 2, catalyst 3, thermal mass flow controllers 4 (MFC, measuring range 6-300 ml/h air for cell fermenter and 2-100 ml/min air for dilution), incubator 5, gas wash bottle 6, sterile filter 7, cell fermenter 8, dilution line 9, stir bar 10, magnetic stirrer 11 with interval function, water bath with heating circuit 12 (37° C.) and sampling and detection device 13. After the catalyst the main stream of carrier gas (air) is divided into completely independent streams (only one stream being shown). The sample diluted with purified air is adsorbed on a multibed sorption tube placed at the outlet of the system.

EXAMPLE

In the performed experiments the bacterial species were purchased from commercial suppliers. Bacteria cells from colonies were inoculated in a liquid preculture and amplified over night at 37° C. The bacteria were cultivated in tryptic soy broth (Merck KGaA, Darmstadt, Germany) and plated on Mueller Hinton agar plates for storage or cell counts. 100 ml of medium in fermenters was inoculated by adding 100 μl of cell suspension of the preculture. As a control not inoculated media in fermenters were prepared.

Headspace samples for GC-MS analysis were taken according to the proliferation features of the tested species at the earliest after certain incubation time (e.g., after 1.5, 2.25, 3, 3.75, 4.5, 5.25, 6, 7.5, 8 h and after 24, 26 and 28 h).

For cultivation of bacteria cells a device was used, which is described in FIG. 1 and allows strictly controlled ventilation.

Volatile metabolites were collected (and simultaneously preconcentrated) by adsorption on solid sorbents placed in glass tubes (see FIG. 1).

For GCMS analysis, the volatile compounds were thermodesorbed and then injected into the GC capillary. A typical GC temperature protocol was: initial 55° C. held for 6 min, then ramped 7° C./min up to 97° C. (2 min), 2° C./min to 110° C. (0 min), 5° C./min to 130° C. (4 min), 5° C./min to 160° C. (4 min), 4° C./min to 230° C. (0 min) and 10° C./min to 280° C. (4 min). The carrier gas helium had a constant flow rate of 2 ml/min.

The detected compounds were identified by the mass spectrum library NIST 2008 (Gaithersburg, Md., USA). Detection was done by spectral library identification and by retention time comparison (with native standards).

The following compounds could be detected in the headspace samples of the respective bacteria.

| Compound name | CAS | Staphylococcus auteus | Pseudomonas aeruginosa | Streptococcus pneumonia | Haemophilus influenzae |
|---|---|---|---|---|---|
| 2-methyl-1-propanol | 78-83-1 | X | | | |
| 2-Ethylacrolein | 922-63-4 | X | | | |
| 2-Methyl-2-butenal (Z) | 1115-11-3 | X | | | |
| Ethyl formate | 109-94-4 | X | | | |
| Ethyl isovalerate | 108-64-5 | X | | | |
| Isopentyl acetate | 123-92-2 | X | | | |
| Hydroxyacetone | 116-09-6 | X | | | |
| 2-butanol | 78-92-2 | | X | | |
| 2-Methylbutyl 2-methyl-butyrate | 2445-78-5 | | X | | |
| 2-Methylbutyl isobutyrate | 2445-69-4 | | X | | |
| amyl isovalerate | 25415-62-7 | | X | | |
| Ethyl 2-methylbutyrate | 868-57-5 | | X | | |
| Isoamyl butyrate | 106-27-4 | | X | | |
| Methyl 2-methylbutyrate | 868-57-5 | | X | | |
| 1,10-Undecadiene | 13688-67-0 | | X | | |
| 10-methyl-1-undecene | 22370-55-4 | | X | | |
| 1-Decene | 872-05-9 | | X | | |
| 1-Nonene | 124-11-8 | | X | | |
| 1-Vinyl aziridine | 5628-99-9 | | X | | |
| 2-Methxy-5-Methylthio-phene | 31053-55-1 | | X | | |
| Mercaptoacetone | 24653-75-6 | | X | | |
| 3-Phenylfuran | 13679-41-9 | | | X | |
| 3-(Methylthio)propanal | 3268-49-3 | | | X | |
| o-Hydroxybenzaldehyde | 90-02-8 | | | | X |
| Methyl Propionate | 554-12-1 | | | | X |
| Vinyl butyrate | 123-20-6 | | | | X |

-continued

| Compound name | CAS | Staphylococcus auteus | Pseudomonas aeruginosa | Streptococcus pneumonia | Haemophilus influenzae |
|---|---|---|---|---|---|
| 2-Acetyl-1,4,5,6-tetra-hydropyridine | 25343-57-1 | | | | X |
| S-Methyl thioacetate | 1534-08-3 | | | | X |
| 3-Methyl-1-butanol | 123-51-3 | X | X | | |
| 2-nonanone | 821-55-6 | | X | X | |
| 3-(ethylthio)-propanal | 5454-45-5 | | X | | X |
| 1-Butanol | 71-36-3 | X | | X | X |
| DMTS | 3658-80-8 | | X | X | X |
| Methyl methacrylate | 80-62-6 | X | X | X | X |
| Dimethyldisulfide | 624-92-0 | X | X | X | X |

Additionally, the following compounds could be detected in the headspace samples of the *Candida albicans*:

| Compound | CAS |
|---|---|
| Ethyl butyrate | 105-54-4 |
| Isopentyl propionate | 106-27-4 |
| 2-methylbutyl acetate | 624-41-9 |
| Vinyl ethyl ether | 109-92-2 |

The invention claimed is:

1. A method of diagnosing an existing or developing acute pneumonia induced by a microorganism comprising:
   a) obtaining a respiratory air sample from a subject,
   b) detecting one or more volatile organic compound(s) in the respiratory air sample without culturing the respiratory air sample prior to the detecting, wherein the volatile organic compound is selected from the group consisting of 2-ethylacrolein, 2-methyl-2-butenal (Z), ethyl formate, ethyl isovalerate, isopentyl acetate, hydroxyacetone, 2-butanol, 2-methylbutyl 2-methylbutyrate, 2-methylbutyl isobutyrate, amyl isovalerate, ethyl 2-methylbutyrate, isoamyl butyrate, methyl 2-methylbutyrate, 1,10-undecadiene, 10-methyl-1-undecene, 1-decene, 1-nonene, 1-vinyl aziridine, mercaptoacetone, 3-phenylfuran, 3-(methylthio)propanal, o-hydroxybenzaldehyde, methyl propionate, vinyl butyrate, 2-acetyl-1,4,5,6-tetrahydropyridine, S-methyl thioacetate, 3-methyl-1-butanol, 3-(ethylthio)-propanal, 1-butanol, dimethyltrisulfide (DMTS), methyl methacrylate, and
   c) administering an effective amount of an antibiotic to the subject when the one or more volatile organic compound(s) in the sample are detected in the respiratory air sample.

2. The method of claim 1, wherein existing or developing acute pneumonia is hospital acquired pneumonia.

3. The method of claim 1, wherein the microorganism is *Pseudomonas aeruginosa, Staphylococcus aureus, Streptococcus pneumoniae* or *Haemophilis influenza*.

4. The method of claim 3, wherein:
   a) one or more volatile organic compound(s) selected from the group consisting of 2-methyl-1-propanol, 2-ethylacrolein, 2-methyl-2-butenal (Z), ethyl formate, ethyl isovalerate, isopentyl acetate and hydroxyacetone is indicative of the presence of *Staphylococcus aureus*; and/or
   b) one or more volatile organic compound(s) selected from the group consisting of 2-butanol, 2-methylbutyl 2-methylbutyrate, 2-methylbutyl isobutyrate, amyl isovalerate, ethyl 2-methylbutyrate, isoamyl butyrate, methyl 2-methylbutyrate, 1,10-undecadiene, 10-methyl-1-undecene, 1-decene, 1-nonene, 1-vinyl aziridine, 2-methoxy-5-methylthiophene and mercaptoacetone is indicative of the presence of *Pseudomonas aeruginosa*; and/or
   c) one or more volatile organic compound(s) selected from the group consisting of 3-phenylfuran and 3-(methylthio)propanal is indicative of the presence of *Streptococcus pneumonia*; and/or
   d) one or more volatile organic compound(s) selected from the group consisting of o-hydroxybenzaldehyde, methyl propionate, vinyl butyrate, 2-acetyl-1,4,5,6-tetrahydropyridine and S-methyl thioacetate is indicative of the presence of *Haemophilus* influenza; and/or
   e) the volatile organic compound 3-methyl-1-butanol is indicative of the presence of *Staphylococcus aureus* and/or *Pseudomonas aeruginosa*; and/or
   f) the volatile organic compound 2-nonanone is indicative of the presence of *Pseudomonas aeruginosa* (B) and/or *Streptococcus pneumonia*; and/or
   g) the volatile organic compound 3-(ethylthio)-propanal is indicative of the presence of *Pseudomonas aeruginosa* and/or *Haemophilus* influenza; and/or
   h) the volatile organic compound 1-butanol is indicative of the presence of *Staphylococcus aureus, Streptococcus pneumoniae* and/or *Haemophilus influenzae*; and/or
   i) the volatile organic compound DMTS is indicative of the presence of *Pseudomonas aeruginosa, Streptococcus pneumoniae* and/or *Haemophilus influenzae*.

5. The method of claim 1, wherein the method further comprises detecting the presence of *Candida albicans*.

6. The method of claim 1, wherein the subject is a mammal.

7. The method of claim 1, wherein an amount or pattern of one or more volatile organic compounds is detected and wherein the amount or pattern is indicative of the degree of the pneumonia.

8. The method of claim 1, wherein the detecting of the compound is performed using a differential mobility.

9. The method of claim 1, further comprising the step
   d) detecting the presence of at least one bacterium selected from the group of *Staphylococcus aureus, Pseudomonas aeruginosa, Streptococcus pneumoniae* and *Haemophilus influenzae* using a method not involving a volatile organic compound.

10. The method of claim 5, wherein the detecting the presence of *Candida albicans* is by detecting the presence of ethyl butyrate, isopentyl propionate, 2-methylbutyl acetate, and/or vinyl ethyl ether.

11. The method of claim 1, wherein the subject is human.

12. The method of claim 1, further comprising a step of identifying the microorganism having infected the subject.

13. The method of claim 12, wherein the step of identifying comprises a method selected from the group consisting of a DNA-based method, an immunoassay-based method, and an immune latex agglutination-based method.

14. The method of claim 1, further comprising detecting 2-nonanone and/or dimethyldisulfide in the subject's respiratory air sample, wherein the presence of 2-nonanone and/or dimethyldisulfide is indicative of the existing or developing acute pneumonia.

15. The method of claim 14, wherein one or more volatile organic compound(s) selected from the group consisting of methyl methacrylate and dimethyldisulfide is indicative of the presence of: *Staphylococcus aureus, Pseudomonas aeruginosa, Streptococcus pneumoniae* and/or *Haemophilus influenza*.

16. A method of detecting one or more volatile organic compound(s) in a subject's respiratory air sample, wherein the volatile organic compound(s) is detected in the respiratory air sample without culturing the respiratory air sample prior to the detecting and wherein the volatile organic compound is selected from the group consisting of 2-ethylacrolein, 2-methyl-2-butenal (Z), ethyl formate, ethyl isovalerate, isopentyl acetate, hydroxyacetone, 2-butanol, 2-methylbutyl 2-methylbutyrate, 2-methylbutyl isobutyrate, amyl isovalerate, ethyl 2-methylbutyrate, isoamyl butyrate, methyl 2-methylbutyrate, 1,10-undecadiene, 10-methyl-1-undecene, 1-decene, 1-nonene, 1-vinyl aziridine, mercaptoacetone, 3-phenylfuran, 3-(methylthio)propanal, o-hydroxybenzaldehyde, methyl propionate, vinyl butyrate, 2-acetyl-1,4,5,6-tetrahydropyridine, S-methyl thioacetate, 3-methyl-1-butanol, 3-(ethylthio)-propanal, 1-butanol, and methyl methacrylate.

17. The method of claim 16, further comprising detecting 2-nonanone and/or dimethyldisulfide and/or dimethyltrisulfide (DMTS) in the subject's respiratory air sample.

18. The method of claim 16, wherein the detecting is by gas chromatography combined with mass spectrometric detection (GC-MS), proton transfer reaction mass spectrometry (PTR-MS), selected ion flow tube mass spectrometry (SIFT-MS), ion mobility spectrometry (IMS), laser spectroscopy, electronic nose or photo acoustic spectroscopy.

19. The method of claim 16, wherein the detecting of the compound is performed using a differential mobility.

20. The method of claim 16, wherein
   a) one or more volatile organic compound(s) selected from the group consisting of 2-methyl-1-propanol, 2-ethylacrolein, 2-methyl-2-butenal (Z), ethyl formate, ethyl isovalerate, isopentyl acetate and hydroxyacetone are detected; and/or
   b) one or more volatile organic compound(s) selected from the group consisting of 2-butanol, 2-methylbutyl 2-methylbutyrate, 2-methylbutyl isobutyrate, amyl isovalerate, ethyl 2-methylbutyrate, isoamyl butyrate, methyl 2-methylbutyrate, 1,10-undecadiene, 10-methyl-1-undecene, 1-decene, 1-nonene, 1-vinyl aziridine, 2-methoxy-5-methylthiophene and mercaptoacetone are detected; and/or
   c) one or more volatile organic compound(s) selected from the group consisting of 3-phenylfuran and 3-(methylthio)propanal are detected; and/or
   d) one or more volatile organic compound(s) selected from the group consisting of o-hydroxybenzaldehyde, methyl propionate, vinyl butyrate, 2-acetyl-1,4,5,6-tetrahydropyridine and S-methyl thioacetate are detected; and/or
   e) the volatile organic compound 3-methyl-1-butanol is detected; and/or
   f) the volatile organic compound 2-nonanone is detected; and/or
   g) the volatile organic compound 3-(ethylthio)-propanal is detected; and/or
   h) the volatile organic compound 1-butanol is detected.

21. The method of claim 17, wherein one or more volatile organic compound(s) selected from the group consisting of methyl methacrylate and dimethyldisulfide are detected.

* * * * *